United States Patent [19]
Fujimoto et al.

[11] Patent Number: 5,386,446
[45] Date of Patent: Jan. 31, 1995

[54] POSITIONAL ADJUSTMENT OF RESOLUTON IN RADIATION CT SCANNER

[75] Inventors: Hideki Fujimoto, Otawara; Yoshinori Manabe, Otawara, both of Japan

[73] Assignee: Kabushiki Kaisha Toshiba, Kawasaki, Japan

[21] Appl. No.: 86,206

[22] Filed: Jul. 6, 1993

[30] Foreign Application Priority Data

Jul. 6, 1992 [JP] Japan .................................. 4-178605
Aug. 5, 1992 [JP] Japan .................................. 4-208638

[51] Int. Cl.$^6$ ............................................. A61B 6/00
[52] U.S. Cl. ............................................. 378/20; 378/8; 378/15
[58] Field of Search .................... 378/4, 8, 11, 15, 16, 378/19, 20, 110, 112, 150–153

[56] References Cited

U.S. PATENT DOCUMENTS

| | | | |
|---|---|---|---|
| 4,174,481 | 11/1979 | Liebetruth | 378/20 |
| 4,630,202 | 12/1986 | Mori . | |
| 4,649,555 | 3/1987 | Matsubayashi | 378/20 X |
| 5,046,003 | 9/1991 | Crawford | 378/20 X |
| 5,090,037 | 2/1992 | Toth et al. | 378/4 |
| 5,103,469 | 4/1992 | Tanaka | 378/20 X |
| 5,212,717 | 5/1993 | Hada | 378/20 X |

Primary Examiner—David P. Porta
Attorney, Agent, or Firm—Oblon, Spivak, McClelland, Maier & Neustadt

[57] ABSTRACT

There provided is a radiation computed tomography (CT) scanner, such as an X-ray CT scaner. A CT image of an object is obtained, resolution of the CT image being affected by a resolution adjustment parameter and the object having an axis. In case of an X-ray CT scaner, the scanner comprises a couch having a longitudinal direction, the axis of the object being aligned along the longitudinal direction, an X-ray source for radiating X-rays toward the object, a detector for detecting the X-rays transmitted through the object, an element for rotating at least the X-ray source around the object, an element for at least relatively moving the X-rays in the longitudinal direction, and an element for controlling the resolution adjustment parameter. Slit members may further be provided for forming the X-rays into a given slice thickness. The parameter includes moving pitches of the couch and rotating element, a rotating speed of the rotating element, an amount of X-rays, and slit widths, according to a longitudinal position of the object.

15 Claims, 7 Drawing Sheets

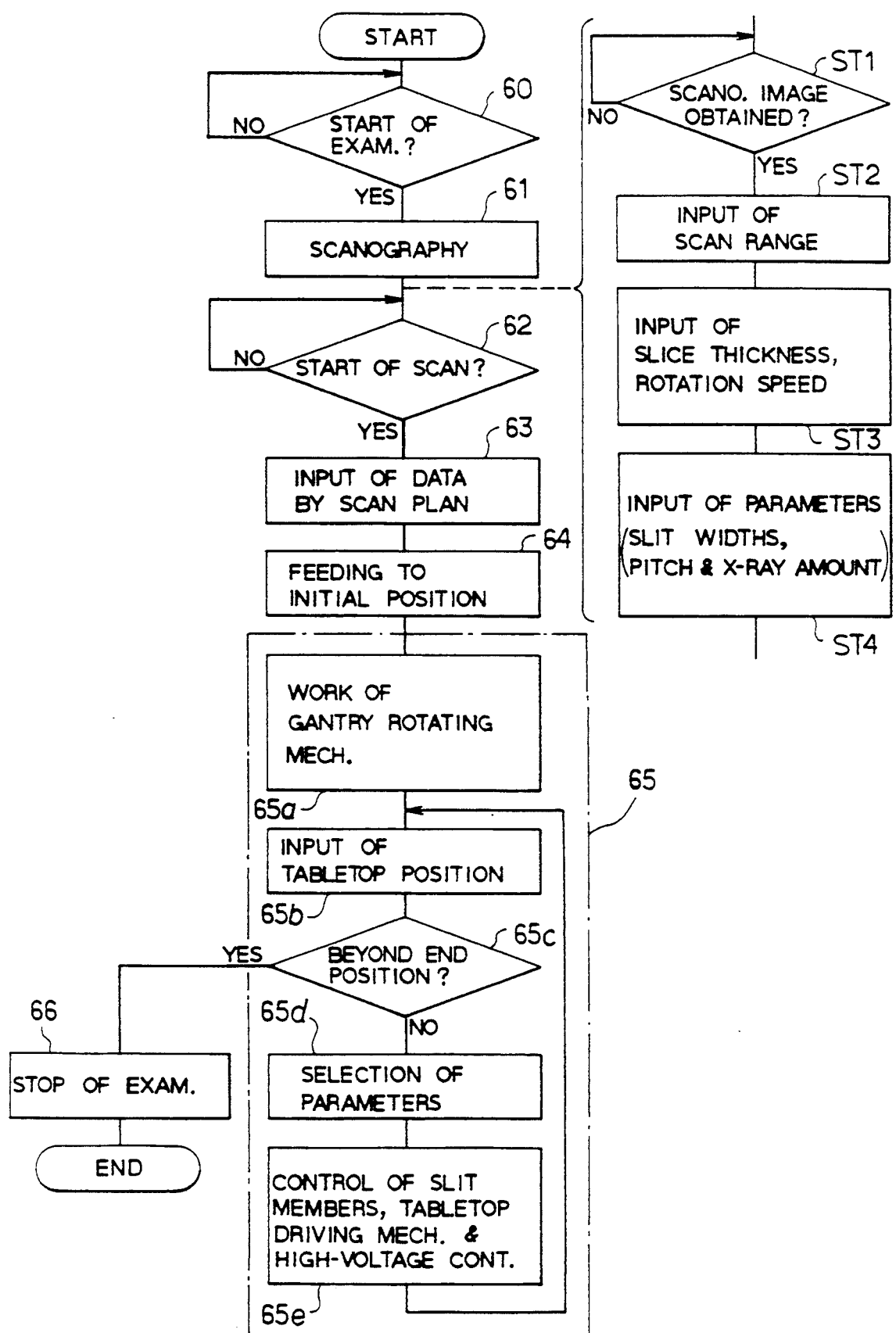
F I G. 4

POSITIONAL ADJUSTMENT OF RESOLUTON IN RADIATION CT SCANNER

BACKGROUND OF THE INVENTION

The present invention relates to a radiation CT (computed tomography) scanner using radiations such as X-rays, and in particular, to a scanner in which spatial resolution can be adjusted in accordance with varying positions along the direction of the body axis of a patient.

An X-ray CT scanner has been widely used to obtain CT images in the medical field. The X-ray CT scanner generally has a gantry in which an X-ray tube and an X-ray detector are arranged for collecting X-ray projected data through a patient placed therebetween. The patient is laid on the tabletop of a couch, the tabletop being movable into an opening in the gantry. Also provided is a tabletop driving mechanism to move the tabletop at a given feeding speed. During examination, as the tabletop moves, the X-ray tube and X-ray detector are rotated around the patient on the basis of a given scan method. The X-ray projected data are sent to an image reconstruction unit, with the result that CT images can be reconstructed and displayed.

In one type of scanning method, a helical scan has been favorably employed. With the helical scan, while the X-ray tube and X-ray detector are rotated, the tabletop is moved along its longitudinal direction toward the opening of the gantry at a feeding speed in accordance with the slice thickness. That is, the X-ray tube and the X-ray detector are helically rotated around the patient.

In the helical scan of an X-ray CT scanner, X-ray projection data are continuously collected over a predetermined scan range in the direction of a patient's body axis (i.e., the longitudinal direction of the tabletop). After the data collection, CT images at any slice position can be reconstructed using the collected data.

In this conventional X-ray CT scanner, upper and lower slit members are disposed at positions close to the radiation output of the X-ray tube and to the input of the X-ray detector, so that the slits of both slit members form an X-ray fan beam having a predetermined slice thickness.

The pitch of the tabletop is selected beforehand depending on a desired slice thickness so as to accomplish continuous slices in the scan range. The "pitch" of the tabletop is used here to mean a distance traveling in its longitudinal direction for each rotation of the X-ray tube and X-ray detector with respect to a patient's body axis. In other words, the pitch is equivalent to the moving speed of the tabletop, though the expression differs.

The quantities, such as slit width, pitch, and amount of X-rays, have an effect on the spatial resolution of the CT images, and hereinafter such quantities, will be referred to as "resolution adjustment parameter".

In the X-ray CT scanner, when a portion having a complex skeleton such as auditory ossicles or a lesion is examined with higher spatial resolution, it is required that the above-mentioned slit widths and pitch be lowered and the amount of X-rays be increased. In contrast, examination of a portion of a non-complex skeleton such as a vertex portion or a portion around a lesion permits lower spatial resolution, thus the slit widths and pitch are large while the X-ray is relatively small.

However, in conventionally-used X-ray CT scanners, the resolution adjustment parameters (the slit widths, pitch, and X-ray amount) are fixed during scanning.

There is thus a problem if an entire head or a wide region containing a lesion is to be examined using a single helical scan.

More specifically, at least one of small slit widths, a small pitch and a large amount of X-rays must be used with the helical scan in order to produce high-resolution images of auditory ossicles or a lesion. However, the drawback is that the scan time becomes longer, which sometimes causes the X-ray tube to exceed its heat capacity rating. This reduces the durability of the scanner. Further, unnecessary X-rays would be exposed to the vertex portion or the surrounding area of the lesion.

When performing CT scanning a patient is usually required to stop breathing during the scan. Where a scan range is mixed with precisely-examined portions and screening-examination portions, resolution adjustment parameters will be in focus on the precisely-examined portions. This will lead to a much longer scan time, and a patient is required to stop breathing for an uncomfortably long time.

On the other hand, when at least one of large slit widths, a large pitch and a small amount of X-rays is selected, it elongates the scan range in the body axis direction of a patient. This results in reducing spatial resolution at the portion of auditory ossicles or a lesion, whose image quality will be poor.

In order to avoid such reciprocity, a number of helical scans could be repeated for each diagnostic portion using different resolution adjustment parameters. But such repetition would cause the entire examination time to be much longer.

SUMMARY OF THE INVENTION

Accordingly, it is a primary object of the present invention to provide a radiation CT scanner, without excessive X-rays exposure, which produces CT images having satisfying resolution in accordance with diagnostic portions and which reduces scan time.

It is a further object of the present invention to provide a radiation CT scanner capable of changing resolution of images depending on the position of the scanner along a patient body axis.

It is a further object of the present invention to easily and precisely specify resolution adjustment parameters at any position along a patient body axis.

It is a still further object of the present invention to provide an X-ray CT scanner having no excessive X-ray exposure, good resolution, and shortened scan time.

It is a still further object of the present invention to apply a helical scan favorably.

These and other objects can be achieved according to the present invention, in one aspect by providing a radiation computed tomography scanner by which a computed tomography image of an object, having an axis to be examined is obtained, resolution of the computed tomography image being affected by a resolution adjustment parameter including a couch on which the object is laid, the axis of the object being aligned along the longitudinal axis of the couch, a radiation source for emitting radiation toward the object laid on the couch, an element for detecting the radiations which have been transmitted through the object, an element for rotating at least the radiation source around the object with respect to the axis of the object, an element for at least relatively moving the scanner in the longitudinal direction, and an element for controlling the resolution adjustment parameter while the moving element moves the scanner.

It is preferred that the scanner further comprises a slit element, which has an adjustable slit width, for forming the radiations into a slice thickness in the longitudinal direction. The slit element has two slit members having adjustable slit widths, respectively, one slit member being arranged between the radiation source and the object and the other slit member being arranged between the object and the detecting element.

Preferably, the scanner is an X-ray CT scanner in which X-rays are used.

It is preferred that the resolution adjustment parameter is determined by at least one of a moving pitch of the couch and/or the rotating element, slit widths of the slit members, an amount of X-rays radiated from the radiation source, and a rotating speed of the rotating means.

It is also preferred that the scanner further comprises a scanning programming unit by which the resolution adjustment parameter is selected according to the positions of a tabletop of the couch.

It is also preferred that the scanner further comprises an element for obtaining data of a scanography image of the object and for supplying the data of the scanography image to the scanning programming unit which displays the scanography image used in the selection of the resolution adjustment parameter.

Further, it is preferred that the rotating element rotates at least the radiation source continuously in a certain rotating direction around the object so as to form helically rotate around the object.

BRIEF DESCRIPTION OF THE DRAWINGS

The accompanying drawings which are incorporated in and constitute a part of this specification, illustrate embodiments of the present invention and, together with the description, serve to explain the principles of the present invention. In the drawings:

FIG. 4 is a flowchart carried out by a control unit in the first embodiment;

DESCRIPTION OF THE PREFERRED EMBODIMENTS

A first embodiment of the present invention will now be described with reference to FIGS. 1 to 5.

Figure 1:
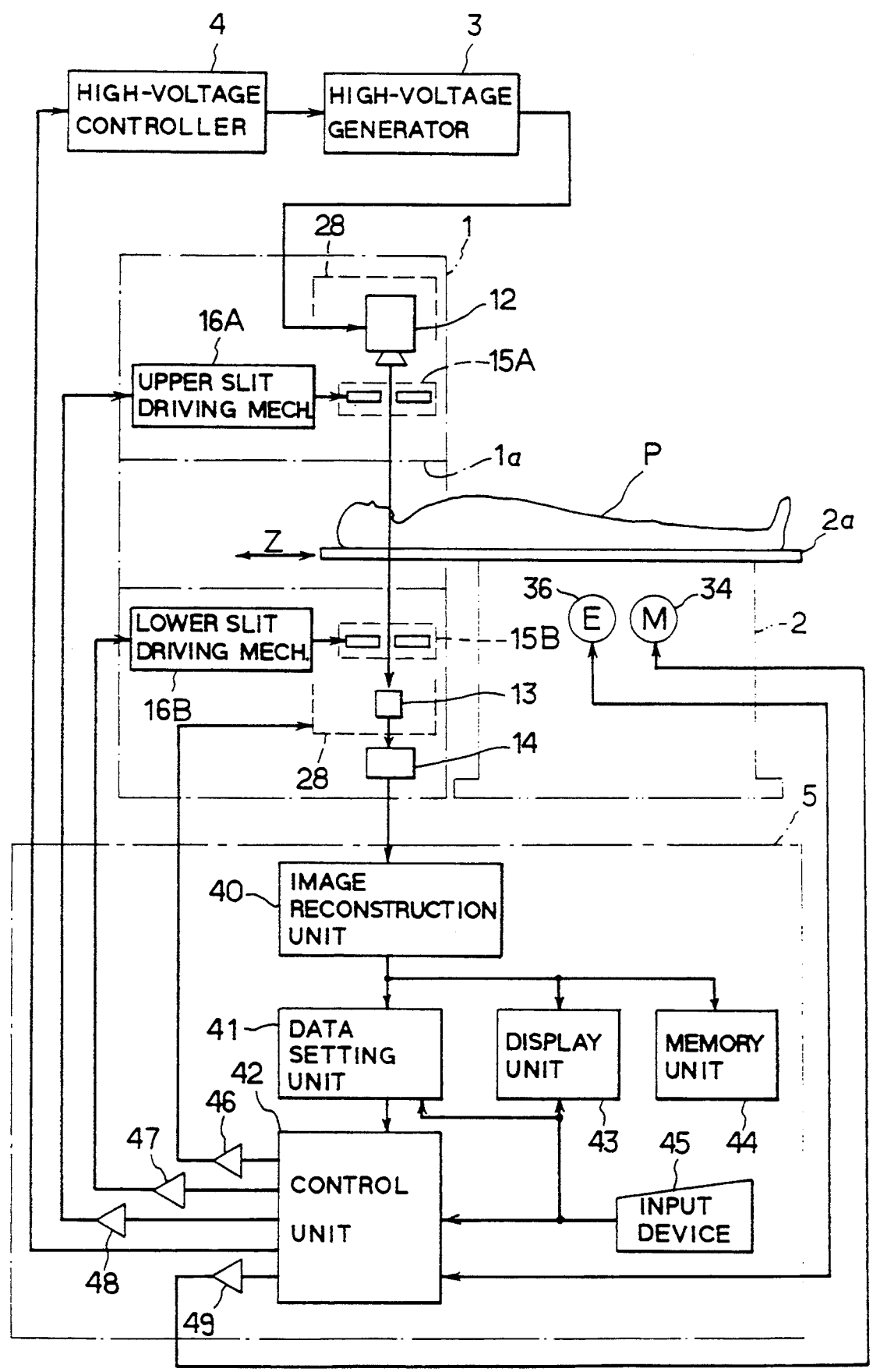
FIG. 1 is a block diagram showing an X-ray CT scanner of a first embodiment of the present invention.

In FIG. 1, there is shown an X-ray CT scanner according to the first embodiment. The X-ray CT scanner comprises a gantry 1, a patient couch 2, a high-voltage generator 3, a high-voltage controller 4 and a console 5. The gantry 1 has an aperture 1a formed therethrough along its axial direction, into which a patient to be examined is inserted. The couch 2 has a tabletop 2a on its top side, a patient P being laid down on the tabletop 2a. The tabletop 2a is formed into a rectangular plate, thus having a longitudinal direction which corresponds to the body axis of the patient P (referred to as the Z-axis in FIG. 1).

In the gantry 1, there are provided an X-ray tube 12 for radiating X-rays at the patient P and an X-ray detector 13 for detecting the X-rays transmitted through the patient P. The X-ray detector 13 is connected to a data acquisition system 14 in the gantry.

Further, there is provided a pair of slit members 15A and 15B in the gantry 1 to form the radiated X-rays into a specified slice thickness. One slit member 15A is arranged at a position close to the X-ray tube 12 in the radiation path and the other slit member 15B is arranged at a position close to the X-ray detector 13 in the radiation path. Hereinafter, the slit member 15A close to the X-ray tube 12 is called "upper slit member" and the slit member 15B close to the X-ray detector 13 "lower slit member".

In the gantry 1, there are further provided upper and lower slit driving mechanisms 16A and 16B to drive each of the upper and lower slit members 15A and 15B.

Figure 2A:
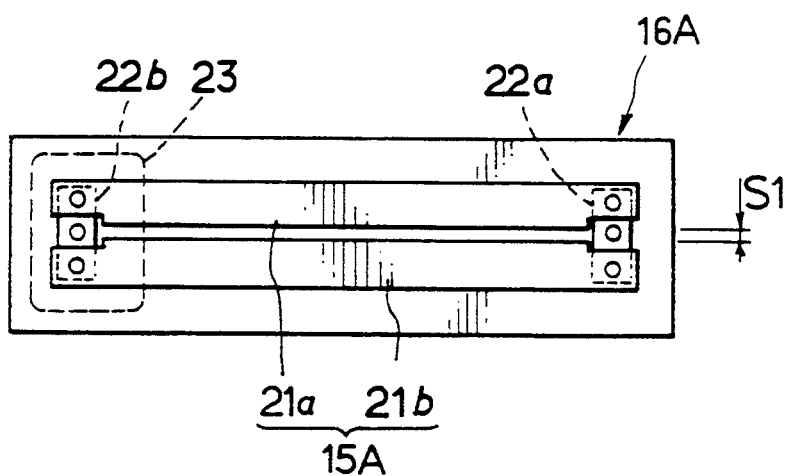
FIG. 2A is a plan view of a unit including an upper slit member.

The upper slit driving mechanism 16A and the upper slit member 15A are practically constructed as a combined unit shown in FIG. 2A. As shown therein, the upper slit member 15A has two slit blades 21a and 21b placed apart from each other in the direction of the body axis of the patient so as to form an adjustable slit width S1, through which the emitted X-rays pass.

The driving mechanism 16A incorporates links 22a and 22b constituting a parallel linkage with the slit blades 21a and 21b and an electric motor 23 coupled with the links 22a and 22b. The motor 23 rotates in response to a driving signal from the console 5, thus adjusting the distance (i.e., the slit width S1) between the slit blades 21a and 21b. Consequently, the slice thickness of an X-ray fan beam is adjustable.

Figure 2B:
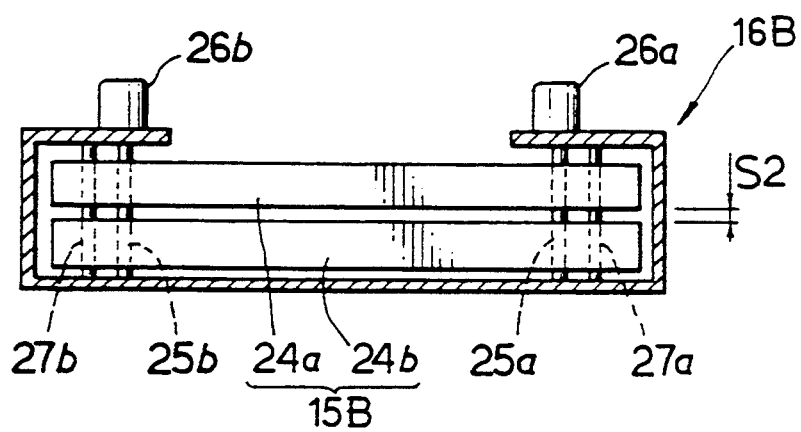
FIG. 2B is a plan view of a unit including a lower slit member.

On the one hand, practically, the lower slit driving mechanism 16B and the lower slit member 15B are also combined in one unit shown in FIG. 2B. The lower slit member 15B has two beam trimming blades 24a and 24b placed apart from each other in the direction of the body axis of the patient so as to form an adjustable slit width S2, through which the emitted X-rays pass.

In the lower slit driving mechanism 16B, supports (not shown) for the beam trimming blades 24a and 24b are incorporated and coupled with each other by means of a threaded connection of lead screws 25a and 25b, respectively. The lead screws 25a and 25b are each coupled with the output shafts of electric motors 26a and 26b receiving driving signals from the console 5. Rotation of the motor 26a and 26b causes the beam trimming blades 24a and 24b to move oppositely to each other in the direction of the body axis of the patient. Consequently, the slit width S2 can be adjusted.

It is desirable that the lead screws 25a and 25b be threaded in opposite directions between one portion coupled with the beam trimming blade 24a and the other portion coupled with the beam trimming blade 24b.

In the lower slit driving mechanism 16B, guides 27a and 27b are slidably inserted through the beam trimming blades 24a and 24b for ensuring their smooth parallel movement.

In the gantry 1, a gantry rotating mechanism 28 is installed for rotating the X-ray tube 12, the X-ray detector 13, the slit driving mechanism 16A and 16B including the slit members 15A and 15B at given spatial positions therein. The gantry rotating mechanism 28, which has a ring-like member for supporting them, is made such that it can be rotated around the aperture 1a in response to a driving signal from the console 5.

Figure 3A:
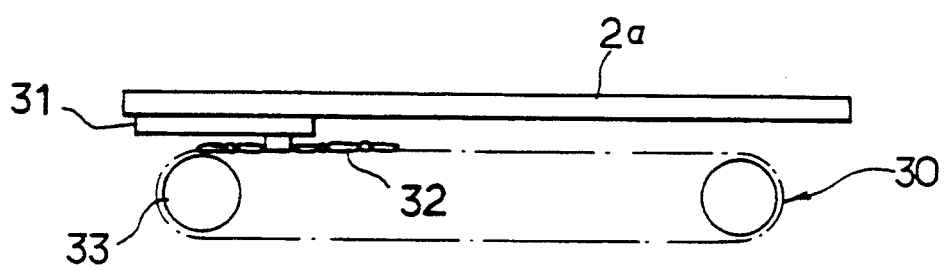
FIG. 3A is a side view of a tabletop driving mechanism.
Figure 3B:
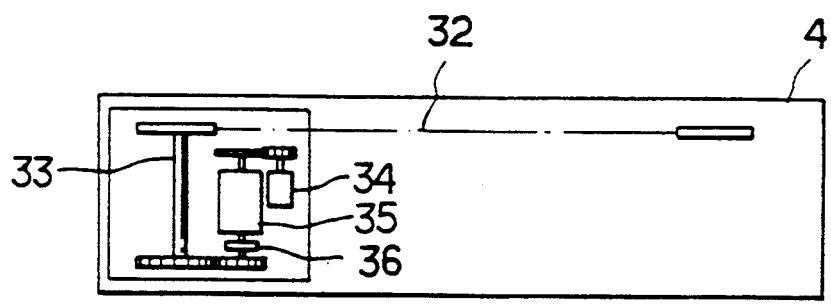
FIG. 3B is a plan view of the tabletop driving mechanism.

The patient couch 2 includes a tabletop driving mechanism 30 for moving the tabletop 2a, as shown in FIGS. 3A and 3B. In the tabletop driving mechanism 30, a movable frame 31 fixedly attached to the tabletop 2a is incorporated to engage with a chain 32. The chain 32 is driven by a driving sprocket 33 which engages with an electric motor 34 through a clutch brake 35. Therefore, the rotation of the motor 34 drives the driving sprocket 33, thus moving the tabletop 2a horizontally in its longitudinal direction. For the motor 34, it is desirable to use a rotation-speed variable type motor including a pulse motor and a servomotor.

An encoder 36 is attached to the axis of the clutch brake 35 in order to detect the longitudinal position of the tabletop 2a. The detected signal from the encoder 36 will be sent to the console 5.

The foregoing high-voltage generator 3 provides the X-ray tube 12 with a specified electric power in response to a signal representing an amount of X-rays. The X-ray amount signal is output from the console 5 via the high voltage controller 4.

Furthermore, the console 5 has an image reconstruction unit 40 connected to the data acquisition system 14, a data setting unit 41 connected to the image reconstruction unit 40, and a control unit 42 connected to the data setting unit 41. Further provided therein are a display unit 43, a memory unit 44, and an input device 45.

Data on the transmitted X-rays which is received by the data acquisition system 14 are sent to the image reconstruction unit 40 for image reconstruction. The image data thus reconstructed are supplied to the data setting unit 41 as well as the display unit 43 and the memory unit 44.

In the data setting unit 41, a scanography image, which will be prepared before helical scan, is produced and the helical scan is programmed. In the helical scan program, by receiving specified tabletop-position data from the input device 45, the slit widths S1 and S2 of the upper and lower slit members 15A and 15B, the pitch of the tabletop 2a, and the amount of X-rays from the X-ray tube 12 are selected as the resolution adjustment parameters, one by one, according to the longitudinal position of the tabletop 2a. A desired scan range is also selected in the scan plan.

The selected data for the helical scan program are sent to the control unit 42 for changing the previous resolution adjustment parameters according to selected values. In order to perform such adjustment, the encoder 36 in the couch 2 is connected to the control unit 42 and its outputs are connected, via servo amplifiers 46 to 49, to the gantry rotating mechanism 28, the slit driving mechanisms 16A and 16B, and the motor 34. For controlling the X-ray amount, the control unit 42 is also connected to the high-voltage controller 4.

The control unit 42 includes a CPU to perform a series of processes depicted in FIG. 4, which will now be described as follows.

In Step 60 of FIG. 4, the control unit 42 waits for an examination start signal from the input device 45, while repeating a judgment as to whether the start signal has been received or not. This judgment will be repeated until a YES response (examination has been ordered) is given. If it has, the processing will then go to Step 61.

In Step 61, a scanography request is made so that a scanography image will be produced. This scanography is performed under the condition that the gantry rotating mechanism 28 is at rest, the X-ray tube 12 and X-ray detector 13 thus being positioned at a predetermined initial position, and the tabletop driving mechanism 30 starts to operate, causing the tabletop 2a to move forward along its longitudinal direction.

Figure 5:
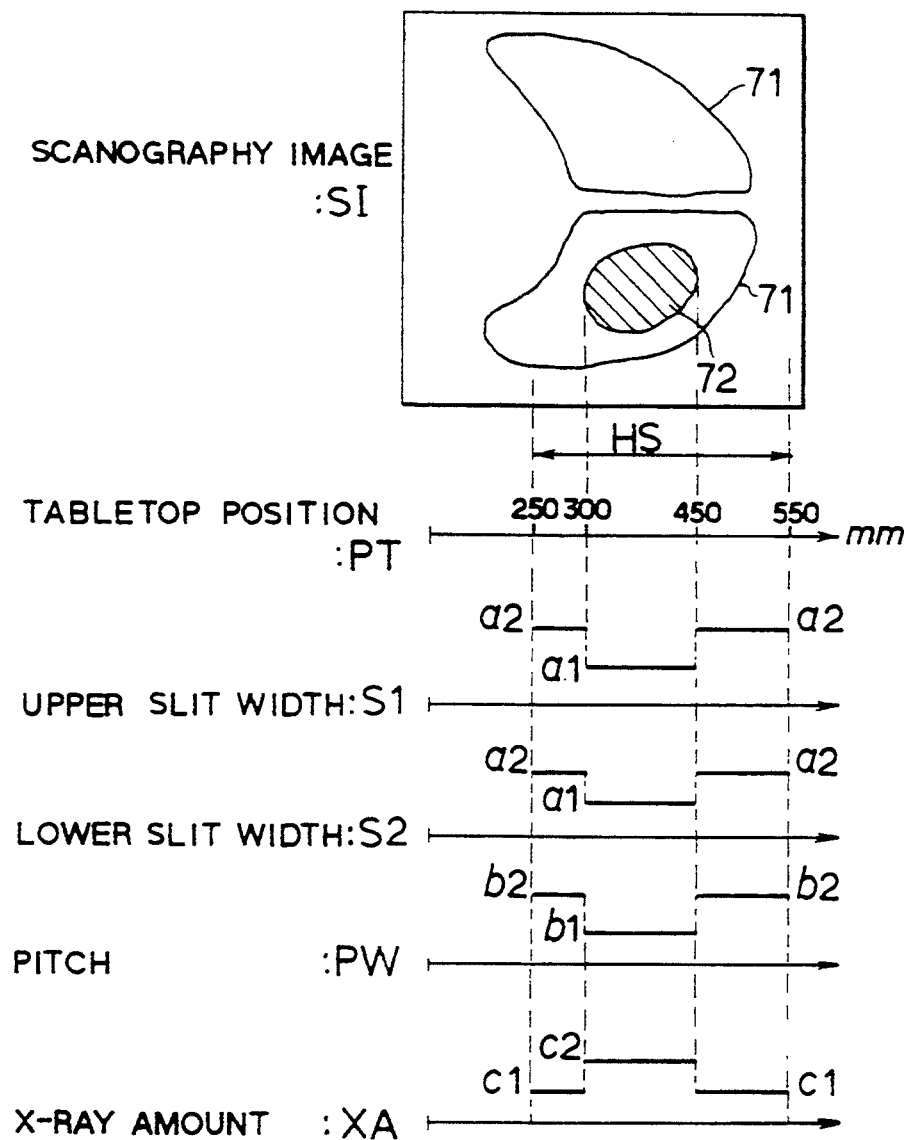
FIG. 5 represents an example of correlation between a scanography image and resolution adjustment parameters.

As a result, data of projected X-rays are received from the image reconstruction unit 40. The projected X-ray data are then sent to the data setting unit 41, the display unit 43, and the memory unit 44. In response to the projected X-ray data, the display unit 43 represents a projected image as a scanography image SI, as shown in FIG. 5. In other words, YES is received in Step ST1 of FIG. 4). At the same time, the projected X-ray data is stored in a memory unit of the data setting unit 41.

Therefore, an operator such as a doctor can see the scanography image SI obtained through a given diagnosis area such as a patient's lungs, which might contain lesions. For instance, the scanography image SI displayed thereon is similar to the image shown in FIG. 5. According to FIG. 5, in the scanography image SI of lungs 71 and 71 of a patient, a lesion 72 is apparent in one of the lungs.

Next, the operator programs a helical scan in Steps ST2 to ST4 of FIG. 4.

First in Step ST2, a desired longitudinal scan range HS is specified using the input device 45 to the data setting unit 41. In the example of FIG. 5, the scan range HS of helical scan is approximately from PT=250 mm to 500 mm.

In Step ST3, data including a desired slice thickness and a rotation speed in accordance with the slice thickness are input using the input device 45 to the data setting unit 41.

Then in Step ST4, by using the input device 45, resolution adjustment parameters consisting of the slit widths S1 and S2, the pitch PW, and the X-ray amount XA are output to the data setting unit 41 in a manner shown in FIG. 5.

That is, for a longitudinal range in the tabletop position of approximately PT=300 mm to 450 mm corresponding to the lesion 72, the slit widths S1, S2 should be reduced down to a value a1, whereas S1, S2=a2 (greater than a1) for the remaining longitudinal ranges surrounding the lesion 72. Also for the range in the tabletop position of approximately PT=300 mm to 450 mm, the pitch PW is reduced down to a level of b1, whereas PW=b2 (greater than b1) for the remaining portion. In contrast, the X-ray amount XA should be raised up to a value c2 for the range of approximately PT=300 mm to 450 mm, but its amount XA down to a value c1 (smaller than c2) for the remaining portion.

In the data setting unit 41, the specified various data and parameters S1, S2, PW and XA are stored. The parameters are stored after being decoded correspondingly one by one to all the positions in a given longitudinal range HS.

Simultaneously with the above helical scan program, the control unit 42 waits for the operator's next command to start the helical scan, while monitoring the process in Step 62.

Hence, when the operator inputs a command to start the helical scan, the control unit 42 is able to determine in Step 62 that the helical scan should begin.

Then, the processing in Steps 63 to Step 66 will be executed in sequence. First, in Step 63, the control unit 42 receives the programmed resolution adjustment parameters stored in the data setting unit 41.

Then in Step 64, by driving the motor 34 in the couch 2 and monitoring the detection signal output from the encoder 36, the control unit 42 brings the tabletop 2a to its specified initial position, i.e., the start position of the scan range HS. This initial position is, for instance, at PT=250 mm shown in FIG. 5.

After the initial setting, in Step 65, the helical scan according to the scan program will be carried out automatically.

First, the gantry rotating mechanism 28 begins operating at a constant rotation speed in accordance with a given slice thickness (Step 65a). Then the longitudinal position PT of the tabletop 2a is detected on the basis of the real-time detection signal from the encoder 36 (Step 65b). Then whether or not the position PT is beyond the outer limit position of the scan range HS is determined (Step 65c). The outer limit position is, for example, PT=550 mm in FIG. 5.

If NO in Step 65c, in response to the detected tabletop position PT, the corresponding resolution adjustment parameters (slit widths S1, S2, pitch PW, and X-ray amount XA) are selected (Step 65d). As a result, in Step 65e, control signals corresponding to the selected parameters are output to the foregoing control objects: the slit driving mechanisms 16A and 16B (i.e., slit members 15A and 15B), the gantry rotating mechanism 28 (i.e., X-ray tube 12 and X-ray detector 13), and the high-voltage controller 4 (i.e., X-ray tube 12).

Steps 65b to 65e are repeated until the a YES judgment is received in Step 65c. When the tabletop position PT goes beyond the outer limit position, the examination is stopped in Step 66 by cutting the control signals which have thus far been output.

Therefore, when the CT examination is initiated, the X-ray tube 12 and X-ray detector 13 are rotated around the patient P and the X-rays, which have a predetermined slice thickness in the direction of the patient body axis, are emitted. Simultaneously with this rotation, the tabletop 2a on which a patient P lies should be moved along its longitudinal direction at a feeding speed determined by the slice thickness.

For the helical scan, all of the slit widths S1, S2, pitch PW, and X-ray amount XA should be adjusted timely and preferably to the predetermined values for each tabletop position over the scan range HS.

Accordingly, the part of the lesion 72 is helically sliced with higher resolution because of smaller slit widths S1, S2, smaller pitch PW, and greater X-ray amount XA, thus being able to obtain more precise X-ray projected data. In contrast, the part surrounding the lesion 72 is helically sliced with appropriate resolution, not higher than that of the lesion 72, by wider slit widths S1 and S2, larger pitch PW, and smaller X-ray amount XA. This makes it possible to avoid excessive X-ray exposure.

In addition, the X-ray CT scanner of the present embodiment adopts a method of slicing only the scan range HS predetermined in the scan program. The scan range HS can be selected, depending on the size of the lesions, by an operator. This makes it possible to avoid unnecessary X-rays being exposed to nonrelated areas representing no medical interest, thereby keeping the amount of radiation to a minimum.

If an object to be scanned is a patient's head, for instance, one can see a portion of the auditory ossicles having a complex skeleton and a portion of the vertex having a rather simple skeleton. Because of this, the resolution adjustment parameters (slit widths, a pitch, and an X-ray amount) corresponding to a higher resolution are allocated to that portion of the auditory ossicles, whereas the parameters of moderate resolution are allocated to that portion of the vertex. Therefore, it is possible to have the same advantages as noted above.

In this embodiment, further, the number of scans may be reduced to one, because the efficiency of the helical scan is higher. According to the conventional helical scan, it has been sometimes required to repeat the scan with different parameters in accordance with the portions to be diagnosed. The X-ray CT scanner of the present invention, by contrast, can greatly reduce the entire imaging time.

Moreover, resolution adjustment parameters can be selected as another form, though the parameters in this embodiment include a combination of slit widths, pitch, and amount of X-rays. For example, it is possible to use a combination of only the slit widths and pitch, or it is possible to use only one of the slit widths, pitch, and amount of X-rays as a parameter.

For the present invention, it is not essential to obtain a scanography image before performing scanning. The procedure of scanography may be omitted, and instead, an operator can directly specify resolution adjustment parameters on the basis of her or his experience.

The moving pitch of the X-ray beam in the longitudinal direction of the couch has been absolutely accomplished by the tabletop. In this respect, it is possible that only the gantry rotating mechanism is moved in the longitudinal direction or both the tabletop and gantry rotating mechanism are moved with respect to each other to produce a relative pitch difference, which is also adjusted according to the tabletop position.

A second embodiment of the present invention will now be described with reference to FIG. 6. The hardware of an X-ray CT scanner is the same as in the first embodiment, and therefore the same reference numerals are used.

In this embodiment, the resolution adjustment parameter is the moving speed of the tabletop 2a (i.e., the pitch in the first embodiment). Therefore, the control unit 42 is designed to carry out the processing shown in FIG. 6.

Figure 6:
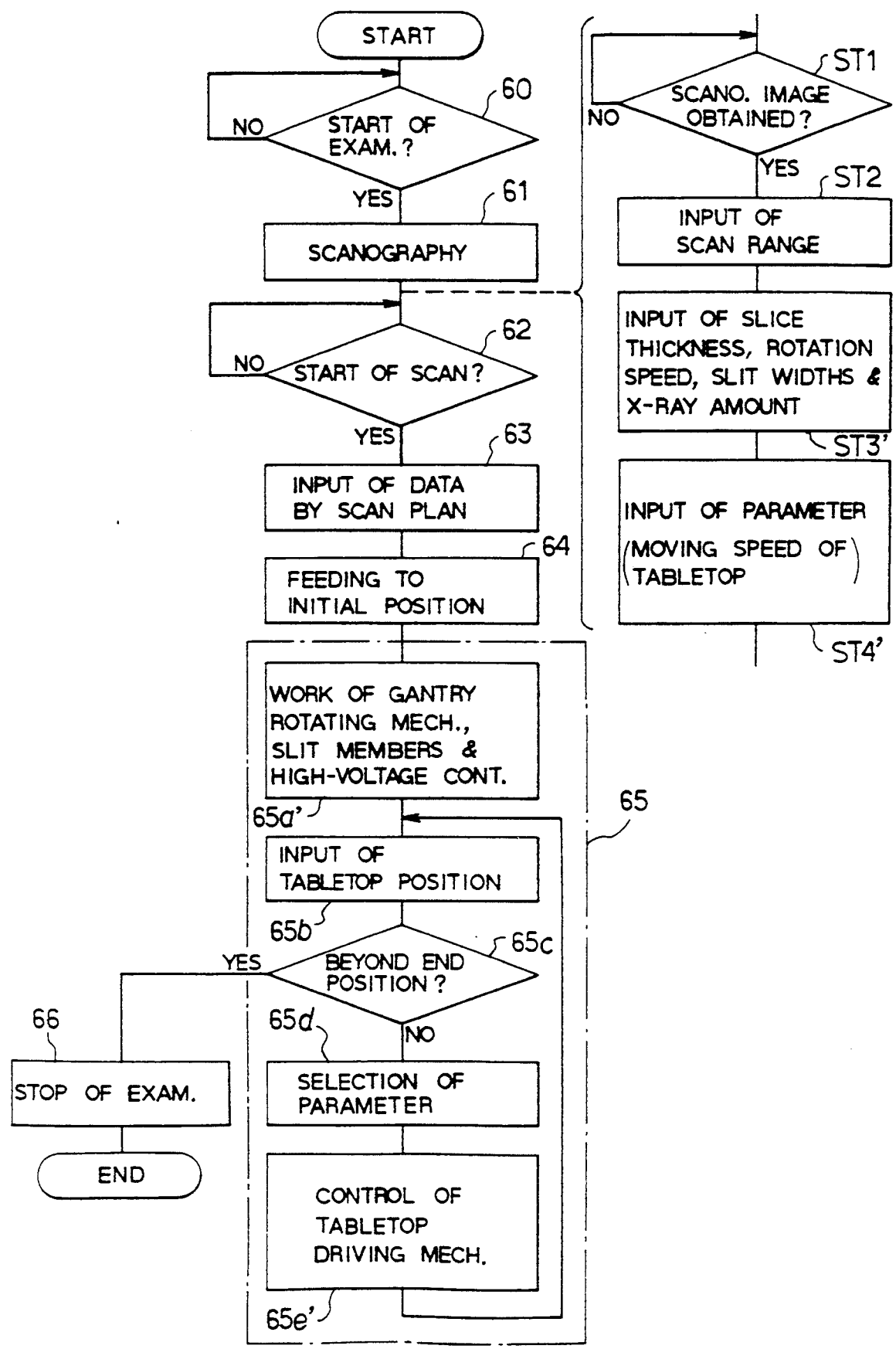
FIG. 6 is a flowchart carried out by a control unit in a second embodiment of the present invention.

In FIG. 6, Steps ST3', ST4', 65a' and 65e' are different from the corresponding Steps in FIG. 4. In Step ST3' not only a slice thickness and a rotation speed of the X-ray tube 12 and X-ray detector 13 but slit widths S1 and S2 and the amount of X-rays are specified as fixed data over a given scan range HS. In Step ST4' as a resolution adjustment parameter, moving speeds of the tabletop 2a are specified, in consideration of the positions and sizes of the lesions on a scanography image, through the input device 45 to the data setting unit 41. If precise-examination portions and screening-examination portions are mixed, a slower speed is given to the precise-examination portions and a faster speed to the screening-examination portions.

On the one hand, in Step 65a', in addition to the gantry rotating mechanism 28, the upper and lower slit members 15A and 15B and the high-voltage controller 4 are operated. In step 65e', in response to the selected moving speed for each of the tabletop positions, the control unit 42 will output a driving signal to the tabletop driving mechanism 30.

This processing enables the tabletop 2a to move at different speeds varying from position to position. That is, for example, for precise-examination portions, it moves slowly if a higher spatial resolution of CT images is desired. For screening-examination portions, on the other hand, it moves faster so as to lead to moderate resolution of CT images.

This embodiment has the following advantages. When helical scanning on patient's lungs is performed by a conventional method whose tabletop moving speed is constant, it requires approximately 30 seconds to perform the examination. To obtain higher quality images requires a patient to stop breathing during imaging period of the scan. Thus the time necessary for the patient to stop breathing is 30 seconds or more, for example. This is difficult for a patient.

In contrast, when a cancer site is found as a precise-examination portion on the lung image, this portion of the patient part is helically scanned at a speed which provides a higher resolution. The remaining portion of the patient is scanned at a speed which is two times faster. As a result, the scan time, that is, the period that the patient has to stop breathing, can be reduced to only 20 seconds, for instance.

For a helical scan of the head of a patient, a portion of the cerebrum can be imaged using a slice thickness such as 5 mm to 10 mm, with almost no artifacts. But, for a portion of the basis cerebri in which skeletons are complicated, it is required that the slice thickness be small, such as 1 mm to 2 mm, to reduce a partial volume effect. However, a constant tabletop speed corresponding to such a small slice thicknesses resulted in much longer scanning time. By applying the present invention, it is possible to combine in slice thickness 1 mm to 2 mm for a portion of the basis cerebri and 5 mm to 10 mm for a portion of the cerebrum. Therefore, this combination makes possible excellent quality images of the portion of the basis cerebri and a shortened scan time.

In addition, the above control of the tabletop speed can be applied to the waist and shoulders of a patient using the helical scan, thus obtaining shortened scanning time and a reduced number of artifacts.

A third embodiment of the present invention will now be described with reference to FIG. 7. The hardware of an X-ray CT scanner is the same in as the first embodiment, and therefore the same reference numerals are used.

In this embodiment, the resolution adjustment parameter is a rotation speed of the gantry rotating mechanism 28 (that is, the X-ray tube 12 and X-ray detector 13). The control unit 42 is designed to carry out the processing shown in FIG. 7.

Figure 7:
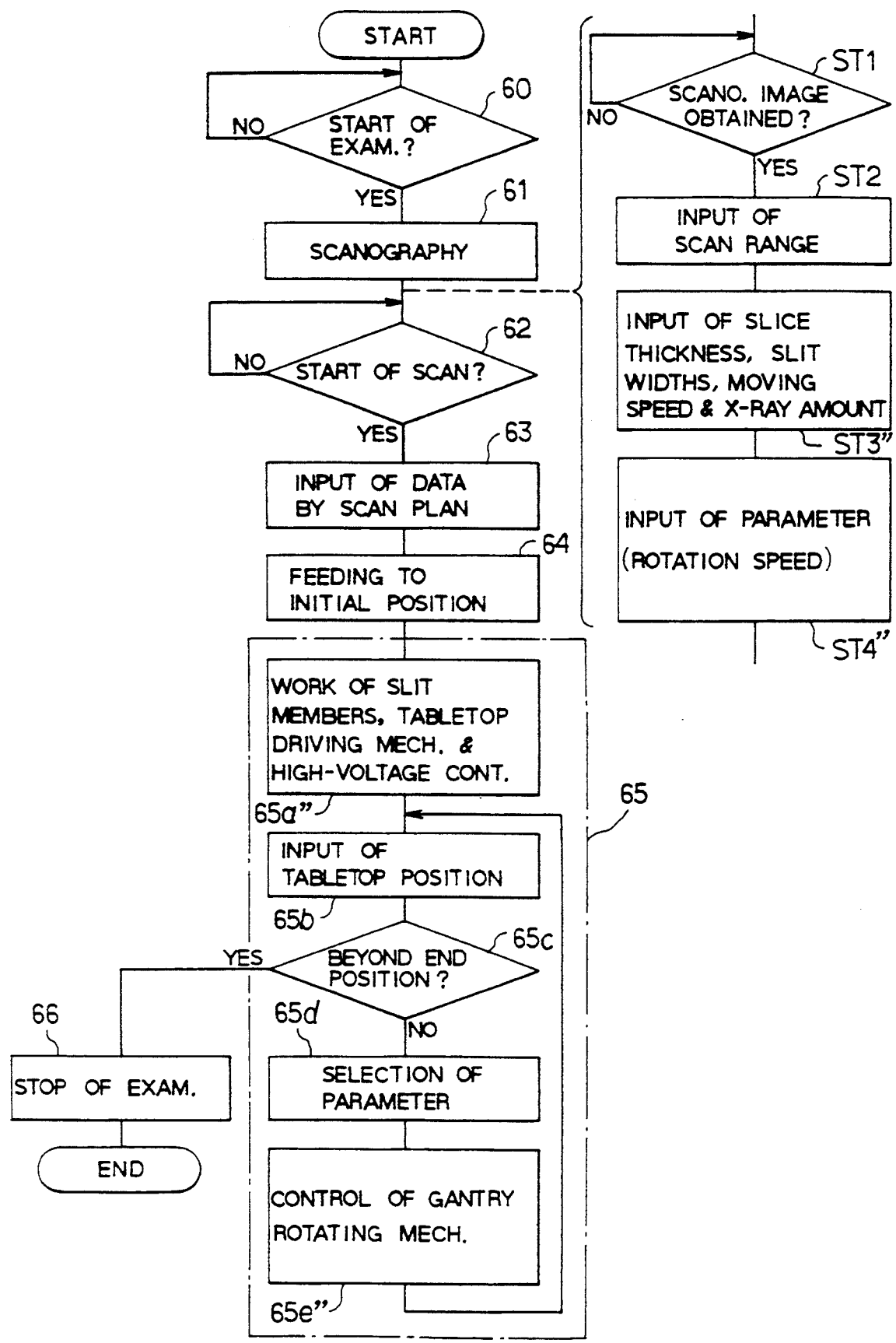
FIG. 7 is a flowchart carried out by a control unit in a third embodiment of the present invention.

In FIG. 7, Steps ST3", ST4", 65a" and 65e" are different from the corresponding Steps in FIG. 4. In Step ST3" a slice thickness, slit widths S1 and S2, a moving speed of the tabletop 2a and an amount of X-rays are specified as fixed data over a given scan range HS. In Step ST4", as a resolution adjustment parameter, rotation speeds of the X-ray tube 12 and X-ray detector 13 are specified, in consideration of lesions on a scanography image. If precise- and screening-examination portions are mixed, a slower speed is allocated to the precise-examination portions and a faster speed to the screening-examination portions.

On the one hand, in Step 65a", the upper and lower slit members 15A and 15B, the tabletop driving mechanism 30, and the high-voltage controller 4 are operated. In Step 65e", in response to a selected rotation speed, the control unit 42 will send a driving signal to the gantry driving mechanism 28.

This processing allows the X-ray tube 12 and the X-ray detector 13 to rotate at different speeds as the tabletop 2a moves. That is, though the tabletop 2a (a patient) moves at a constant speed, the rotation speed of the X-ray fan beam changes from range to range. This is an equivalent helical scan as the second embodiment, yielding the same advantages as noted above.

The above embodiments have been described with regard to a helical scan, but the present invention is not limited to this. For example, scanning during which an X-ray source is rotated alternately in clockwise and counterclockwise directions is also possible. With this type of scan, a rotation angle of less than 360 degrees (for instance, 200 degrees) is acceptable.

The present invention is applicable to an X-ray scanner in which only an X-ray tube is constructed to be rotated around a patient and in which an X-ray detector is fixed.

Further, in the fifth-generation system of an X-ray CT system, an X-ray source is constructed such that an X-ray tube is fixedly arranged but a focus point therein is moved, so that the X-ray source rotates around a patient. This system is intended to be covered by the present invention as well.

Furthermore, the present invention may be applied to X-ray CT scanners in which a two-dimensional array type X-ray detector is used instead of the above one-dimensional detector, or a plurality of X-ray sources are arranged around the patient.

As to the types of radiation sources to be used, it is possible to use a pellet containing a radioisotope radiating X-rays, a device radiating X-rays by accelerating electron beams by a accelerator, or an X-ray laser apparatus.

The present invention may also be applied to a gamma-ray CT scanner.

What we claim is:

1. A radiation computed tomography scanner by which a computed tomography image of an object to be examined is obtained by a helical scan, resolution of the computed tomography image being affected by a resolution adjustment parameter, the scanner comprising:
   a couch for supporting the object having a body axis, said object being examined along a direction of the body axis;
   a radiation source for emitting radiation toward the object laid on the couch so that the radiation is transmitted through the object;
   means for detecting the radiation transmitted through the object;
   means for driving the radiation source and the couch which are relatively rotatable with respect to each other and relatively linearly movable with respect to each other along the direction of the body axis in order to perform the helical scan; and
   means for controlling the resolution adjustment parameter simultaneously with performing the helical scan.

2. The scanner according to claim 1, wherein said couch has a tabletop on which the object is laid, the tabletop representing a longitudinal direction along which the direction of the body axis is aligned and being movable along the longitudinal direction.

3. The scanner according to claim 2, wherein said driving means comprises means for rotating the radiation source and the detecting means together along a circular locus around the object and means for moving the tabletop in the longitudinal direction while the radiation source and the detecting means are rotated together by the rotating means.

4. The scanner according to claim 3, further comprising a slit means, which has an adjustable slit width, for projecting the radiation as a slice thickness in the longitudinal direction.

5. The scanner according to claim 4, wherein said resolution adjustment parameter comprises at least one of a moving pitch of the tabletop, the slit width of the slit means, an amount of radiation emitted from the radiation source, and a rotating speed of the radiation source and the detecting means.

6. The scanner according to claim 5, wherein said slit means has two slit members having adjustable slit widths, respectively, one slit member being arranged between the radiation source and the object and the other slit member being arranged between the object and the detecting means.

7. The scanner according to claim 6, wherein said radiation source is an X-ray tube for emitting X-rays.

8. The scanner according to claim 3, wherein said resolution adjustment parameter comprises at least one of a moving pitch of the tabletop in the longitudinal direction, an amount of radiation emitted from the radiation source, and a rotating speed of the radiation source and the detecting means.

9. The scanner according to claim 8, wherein said radiation source comprises an X-ray tube which emits X-rays.

10. The scanner according to claim 8, wherein said controlling means comprises means for measuring a time corresponding to a position of the tabletop in the longitudinal direction and means for changing the resolution adjustment parameter in response to the time measured by the time measuring means.

11. The scanner according to claim 8, wherein said controlling means comprises a detector for detecting a position of the tabletop in the longitudinal direction and means for changing the resolution adjustment parameter in response to the position of the tabletop detected by the detector.

12. The scanner according to claim 11, further comprising means for programming the helical scan which has a selecting means for selecting the resolution adjustment parameter manually for each of a plurality of positions of the tabletop in the longitudinal direction, the selected adjustment parameter being output to the changing means.

13. The scanner according to claim 12, further comprising means for obtaining data of a scanography image of the object, the data of the scanography image being supplied to the programming means, wherein said programming means includes a display means which displays the scanography image which is used in the selection of the resolution adjustment parameter.

14. The scanner according to claim 13, wherein said programing means has an input means for manually inputting a scan range in the longitudinal direction and the selecting means includes means for selecting the resolution adjustment parameter within the scan range.

15. The scanner according to claim 14, wherein said programming means has a further input means for manually specifying a range corresponding to a region of interest within the scan range on the scanography image displayed on the display means and said selecting means has an additional means for assigning the range of the resolution adjustment parameter of a higher resolution grade than an outer limit of the range in the longitudinal direction.

* * * * *